US010817993B2

(12) United States Patent
Takahashi

(10) Patent No.: US 10,817,993 B2
(45) Date of Patent: Oct. 27, 2020

(54) RADIOGRAPHIC IMAGING SYSTEM AND RADIOGRAPHIC IMAGING METHOD

(71) Applicant: CANON KABUSHIKI KAISHA, Tokyo (JP)

(72) Inventor: Naoto Takahashi, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/725,156

(22) Filed: Oct. 4, 2017

(65) Prior Publication Data
US 2018/0108118 A1    Apr. 19, 2018

(30) Foreign Application Priority Data

Oct. 17, 2016  (JP) ................................ 2016-203476

(51) Int. Cl.
*G06T 9/00*  (2006.01)
*G06T 5/00*  (2006.01)
(Continued)

(52) U.S. Cl.
CPC ............ *G06T 5/005* (2013.01); *A61B 6/4266* (2013.01); *A61B 6/5235* (2013.01); *G01N 23/04* (2013.01);
(Continued)

(58) Field of Classification Search
CPC ....... A61B 6/5241; A61B 6/54; A61B 6/5235; A61B 6/566; A61B 6/4266; A61B 6/4441; A61B 5/08; A61B 6/4291; A61B 6/5211; A61B 6/4035; A61B 1/041; G06T 2207/30004; G06T 2207/30196; G06T 7/90; G06T 2207/10116; G06T 5/005; G06T 2207/20216; G06T 2207/30008;
(Continued)

(56) References Cited

U.S. PATENT DOCUMENTS

| 5,981,968 A | * | 11/1999 | Nakazawa ........... A61B 6/4216 250/587 |
| 2002/0039401 A1 | * | 4/2002 | Salb .................... A61B 6/4241 378/98.9 |

(Continued)

FOREIGN PATENT DOCUMENTS

| JP | 2005-505960 A | 2/2005 |
| JP | 2016-140515 A | 8/2016 |

*Primary Examiner* — Aklilu K Woldemariam
(74) *Attorney, Agent, or Firm* — Canon U.S.A., Inc. IP Division

(57) ABSTRACT

A radiographic imaging system and imaging method that improves image quality of a combined image including a defective region caused by a structural object of a radiation detection apparatus are provided. The radiographic imaging system, which includes a plurality of radiation detection apparatuses that detect radiation and a combining processing unit that combines a plurality of radiographic images acquired from the plurality of radiation detection apparatuses to generate a combined image, corrects a pixel value of a correction target pixel of a region in which a structural object of a radiation detection apparatus is included in the combined image using a pixel value of a pixel in a range predetermined with reference to the correction target pixel of a region in which the structural object is not included in the combined image.

16 Claims, 12 Drawing Sheets

(51) Int. Cl.
  *A61B 6/00* (2006.01)
  *G01N 23/04* (2018.01)
  *G06T 5/50* (2006.01)

(52) U.S. Cl.
  CPC ...... *G06T 5/50* (2013.01); *G06T 2207/10116* (2013.01); *G06T 2207/20216* (2013.01); *G06T 2207/30004* (2013.01); *G06T 2207/30008* (2013.01)

(58) Field of Classification Search
  CPC ........... G06T 5/20; G06T 5/50; G06T 7/0012; G06T 7/248; H04N 5/23293; H04N 5/32; H04N 5/3535; H04N 5/347; H04N 5/23238; H04N 5/367; H04N 2005/2255; H04N 2209/045; G01N 23/04; G06K 9/00362; G06K 9/00597; G06F 19/321; G01T 1/16; G01T 7/00; G01V 5/005; H01L 27/14658
  USPC ......... 382/128, 129, 130, 131, 132; 348/246
  See application file for complete search history.

(56) References Cited

U.S. PATENT DOCUMENTS

| | | | | |
|---|---|---|---|---|
| 2005/0238217 | A1* | 10/2005 | Enomoto | G06K 9/00597 382/128 |
| 2006/0017826 | A1* | 1/2006 | Sekimoto | A61B 1/041 348/246 |
| 2007/0065038 | A1* | 3/2007 | Maschauer | H04N 5/2355 382/274 |
| 2008/0012967 | A1* | 1/2008 | Kuwabara | G06T 5/005 348/246 |
| 2008/0019580 | A1* | 1/2008 | Ohyu | G06K 9/3216 382/130 |
| 2009/0080749 | A1* | 3/2009 | Visser | G06T 5/50 382/131 |
| 2009/0135452 | A1* | 5/2009 | Matsuura | H04N 1/19515 358/450 |
| 2009/0296883 | A1* | 12/2009 | Saito | G06T 5/008 378/62 |
| 2010/0215243 | A1* | 8/2010 | Ohno | A61B 6/4035 382/132 |
| 2010/0246921 | A1* | 9/2010 | Iwami | G06T 5/008 382/132 |
| 2011/0233411 | A1* | 9/2011 | Nishino | G01T 1/2018 250/361 R |
| 2012/0182323 | A1* | 7/2012 | Omi | H04N 5/32 345/660 |
| 2013/0068955 | A1* | 3/2013 | Matsuura | G01T 1/247 250/370.09 |
| 2013/0077744 | A1* | 3/2013 | Kamiya | A61B 6/548 378/62 |
| 2013/0156285 | A1* | 6/2013 | Hayashida | G06T 5/20 382/132 |
| 2013/0259334 | A1* | 10/2013 | Otsuka | G06T 5/008 382/128 |
| 2014/0112448 | A1* | 4/2014 | Takenaka | H04N 5/32 378/114 |
| 2014/0185903 | A1* | 7/2014 | Fukuda | A61B 6/502 382/132 |
| 2014/0205066 | A1* | 7/2014 | Kitagawa | A61B 6/542 378/62 |
| 2014/0291541 | A1* | 10/2014 | Watanabe | H04N 5/367 250/394 |
| 2014/0294277 | A1* | 10/2014 | Katsumata | G06T 5/007 382/132 |
| 2015/0055752 | A1* | 2/2015 | Takahashi | H04N 5/32 378/62 |
| 2015/0243045 | A1* | 8/2015 | Ra | A61B 6/032 382/131 |
| 2016/0098836 | A1* | 4/2016 | Yamato | A61B 6/50 382/128 |
| 2016/0220211 | A1* | 8/2016 | Yamada | A61B 6/4208 |
| 2016/0227130 | A1* | 8/2016 | Takekoshi | A61B 6/54 |
| 2017/0079610 | A1* | 3/2017 | Morf | A61B 6/469 |

* cited by examiner

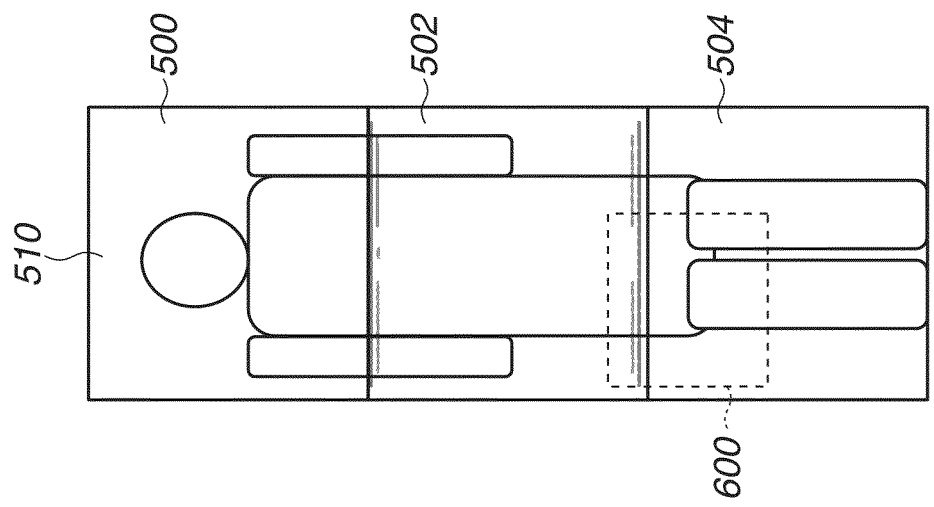
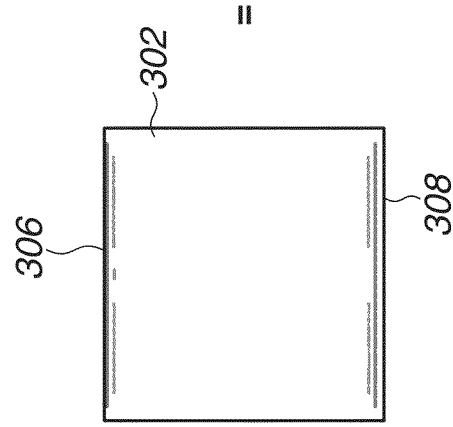
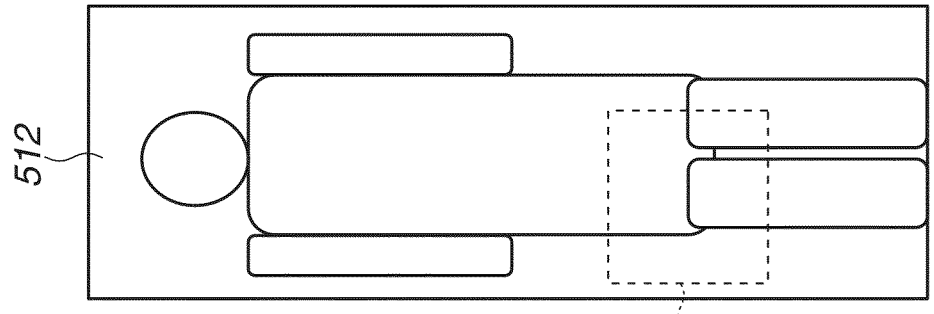

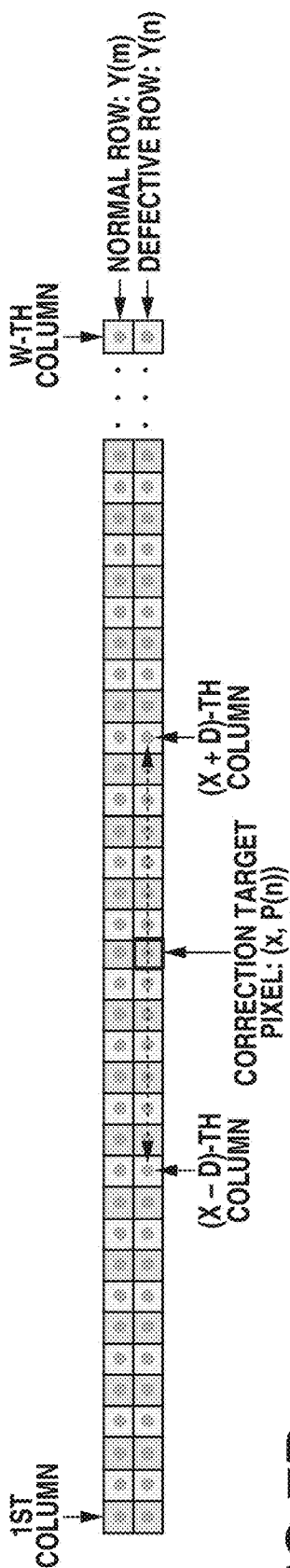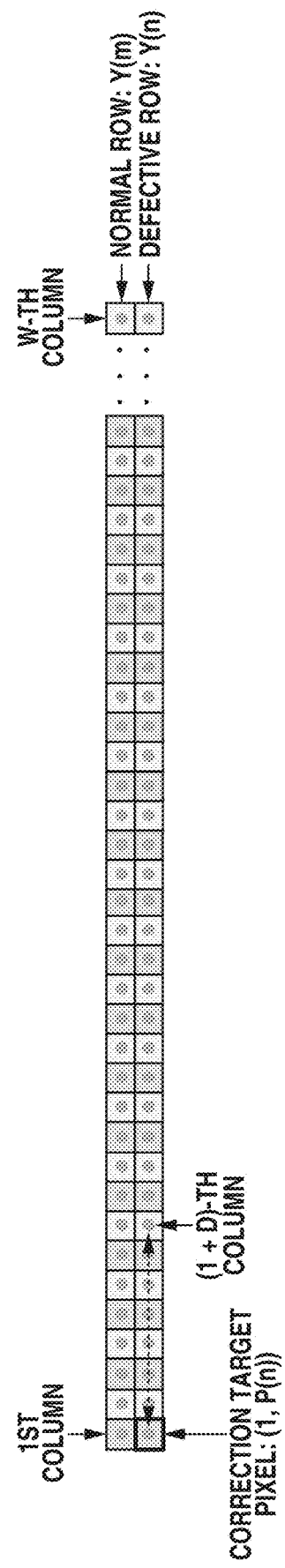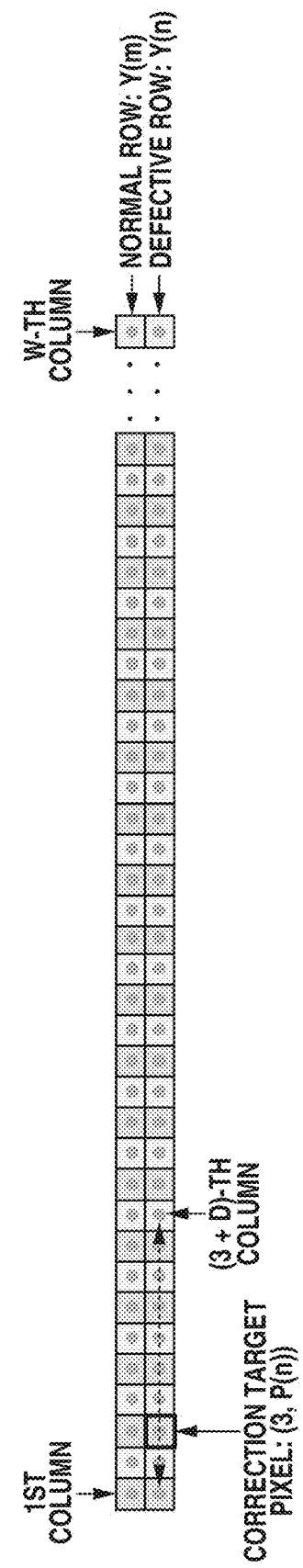

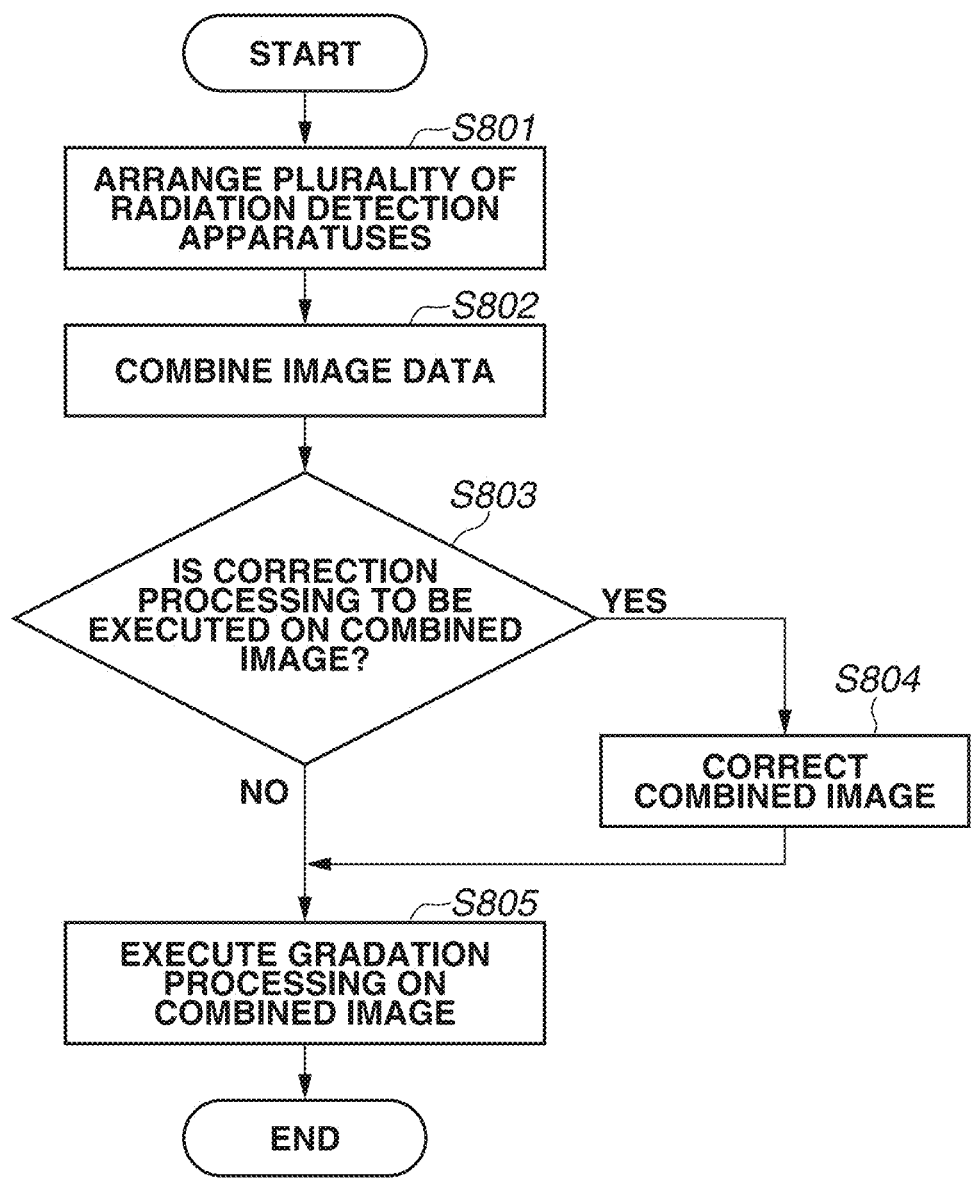

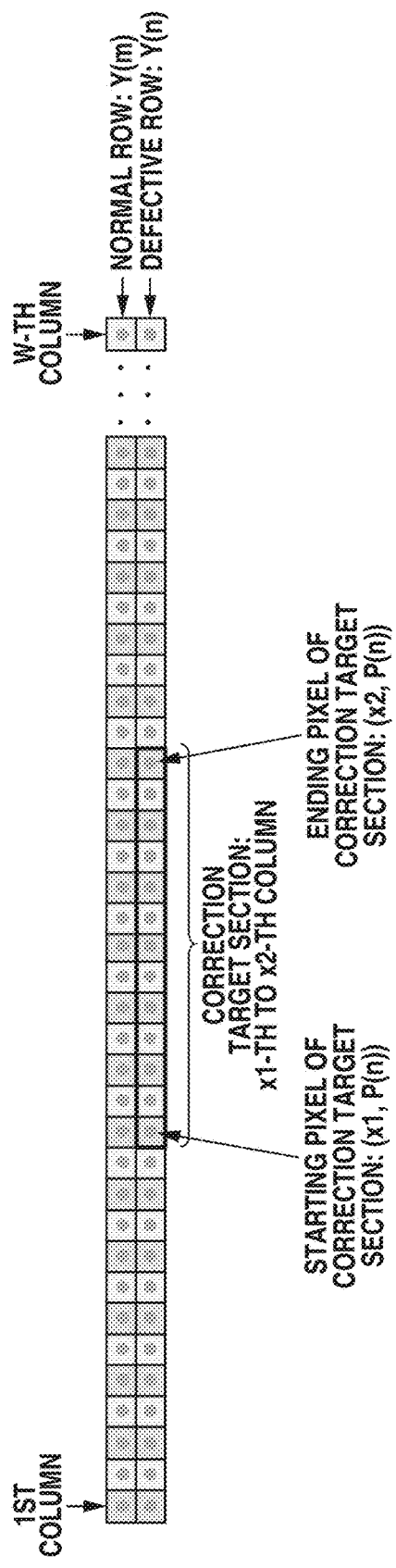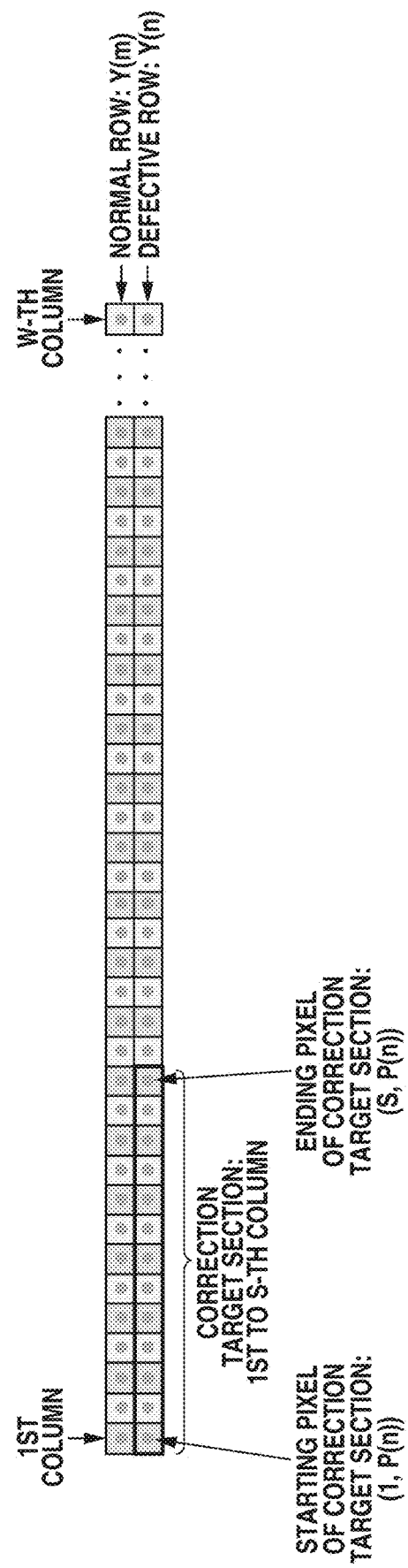

RADIOGRAPHIC IMAGING SYSTEM AND RADIOGRAPHIC IMAGING METHOD

BACKGROUND

Field

The present disclosure relates to a radiographic imaging system that executes imaging using radiation and a radiographic imaging method.

Description of the Related Art

In the medical field, imaging of, in particular, the entirety of the spine, the lower limb, or the body of a subject, has been performed. Such imaging is performed for a wide observation area (hereinafter, referred to as "long-length imaging"). Japanese Patent Application Laid-Open No. 2016-140515 discusses a radiographic imaging system that executes long-length imaging by arranging a plurality of radiation detection apparatuses (radiographic imaging apparatuses) and corrects a structural object, of the radiation detection apparatuses overlapping with each other, including in a long-length image (combined image).

In a method described in Japanese Patent Application Laid-Open No. 2016-140515, because a defective row of an area in which a structural object includes is corrected by a row unit, there is a possibility that the defective row cannot be corrected appropriately depending on a distribution state of pixel values of the defective row.

SUMMARY

The present disclosure is directed to a radiographic imaging system and a radiographic imaging method that improves image quality of a combined image including a defective region caused by a structural object of a radiation detection apparatus. According to an aspect of the present disclosure, a radiation imaging system including a plurality of radiation detection apparatuses that detect radiation and a combining processing unit that combines a plurality of radiographic images acquired from the plurality of radiation detection apparatuses to generate a combined image, the radiographic imaging system includes an image correction unit configured to correct a pixel value of a correction target pixel of a region in which a structural object of a radiation detection apparatus is included in the combined image using a pixel value of a pixel in a range predetermined with reference to the correction target pixel of a region in which the captured structural object is not included in the combine image.

Further features will become apparent from the following description of exemplary embodiments with reference to the attached drawings.

BRIEF DESCRIPTION OF THE DRAWINGS

FIGS. 5A, 5B, and 5C are diagrams illustrating an example of correction processing executed by an image correction unit of the radiographic imaging system.

FIGS. 7A, 7B, and 7C are diagrams illustrating examples of correction processing executed by the image correction unit of the radiographic imaging system.

FIG. 9 is a flowchart illustrating processing of the radiographic imaging system.

FIGS. 10A and 10B are diagrams illustrating examples of correction processing executed by the image correction unit of the radiographic imaging system in a second exemplary embodiment.

DESCRIPTION OF THE EMBODIMENTS

Hereinafter, exemplary embodiments will be described with reference to the appended drawings.

Figure 1:
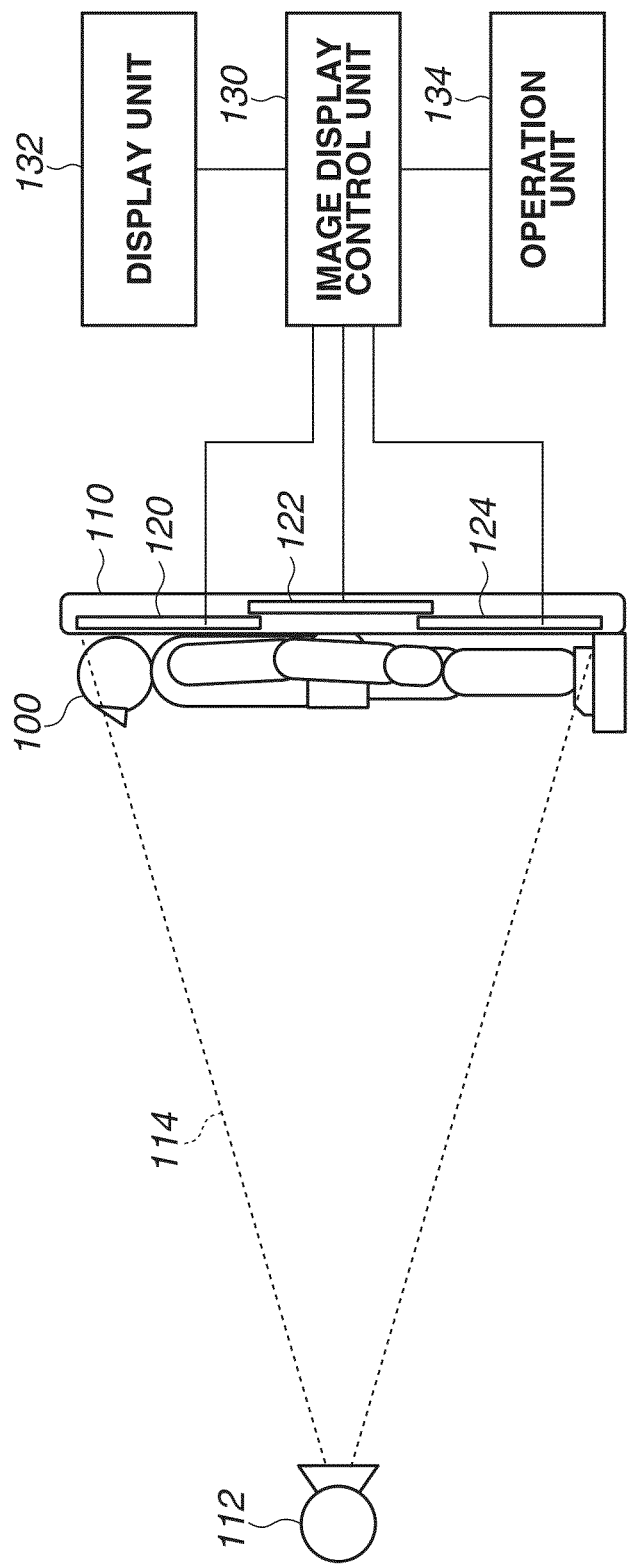
FIG. 1 is a diagram illustrating a schematic configuration of a radiographic imaging system.

FIG. 1 is a diagram schematically illustrating a configuration of a radiographic imaging system an exemplary embodiment. A schematic configuration of the radiographic imaging system in which a plurality of radiation detection apparatuses are arranged to execute long-length imaging is illustrated in FIG. 1.

The radiographic imaging system includes a radiation generation unit 112 for generating radiation. The radiation generation unit 112 can emit radiation in an irradiation range 114. The radiation generation unit 112 is disposed via a supporting unit (not illustrated) provided on a floor or a ceiling. A diaphragm (not illustrated) for shielding radiation is arranged on an irradiation face of the radiation generation unit 112. An operator controls the diaphragm for shielding radiation to set the irradiation range 114 of radiation emitted from the radiation generation unit 112.

The radiographic imaging system includes a plurality of radiation detection apparatuses 120, 122, and 124. Herein, although the radiation imaging system including three radiation detection apparatuses 120, 122, and 124 will be described, the number of radiation detection apparatuses can be more or less than three. The plurality of radiation detection apparatuses 120, 122, and 124 detects the radiation passing through a subject 100 and outputs image data based on the radiation. The image data can also be referred to as a radiographic image.

Specifically, the radiation detection apparatuses 120, 122, and 124 detect the radiation passing through the subject 100 as electric charges corresponding to the amount of transmitted radiation. For example, a direct conversion sensor using an amorphous selenium (a-Se) semiconductor that directly converts radiation into electric charges or an indirect sensor using a scintillator such as a cesium iodide (CsI) scintillator and a photoelectric conversion element consisting of an amorphous silicon (a-Si) semiconductor is used for the radiation detection apparatuses 120, 122, and 124. The radiation detection apparatuses 120, 122, and 124 generate image data by executing analog-digital (A/D) conversion of detected electric charges, and output the image data to the image display control unit 130.

The radiation detection apparatuses 120, 122, and 124 are set inside the imaging table 110. The imaging table 110 is a rectangular-shaped hollow housing. The imaging table 110 holds the radiation detection apparatuses 120, 122, and 124.

As illustrated in FIG. 1, the imaging table 110 is installed in an upright position with respect to the floor. The subject 100 is arranged along a lengthwise direction of the imaging table 110. The imaging table 110 supports the subject 100.

In FIG. 1, the imaging table 110 is disposed in the upright position with respect to the floor, so that the lengthwise direction of the imaging table 110 is in a vertical direction. The imaging table 110 can be disposed parallel to the floor, to make the lengthwise direction of the imaging table 110 in a horizontal direction.

The radiation detection apparatuses 120, 122, and 124 are arranged on the imaging table 110 in the lengthwise direction of the imaging table 110. In this arrangement, the radiation detection apparatuses 120, 122, and 124 are disposed so that the radiation detection apparatuses 120, 122, and 124 partly overlap each other. For example, as illustrated in FIG. 1, the radiation detection apparatuses 120 and 122 are disposed so that a part of the radiation detection apparatus 120 and a part of the radiation detection apparatus 122 spatially overlap each other. In this arrangement, imageable regions of the radiation detection apparatuses 120 and 122 overlap each other. Similarly, the radiation detection apparatuses 122 and 124 are disposed so that a part of the radiation detection apparatus 122 and a part of the radiation detection apparatus 124 spatially overlap each other. In this arrangement, imageable regions of the radiation detection apparatuses 122 and 124 overlap each other. The radiation detection apparatus 122 is disposed on a backside of the radiation detection apparatuses 120 and 124, at a position farther from the radiation generation unit 112 than the radiation detection apparatuses 120 and 124.

The radiographic imaging system includes an image display control unit 130 that executes image processing on the image data output from the radiation detection apparatuses 120, 122, and 124 to generate an image, a display unit 132 for displaying the image, and an operation unit 134 for receiving an instruction from an operator. The image display control unit 130 controls each constituent element.

The image display control unit 130 is connected to the radiation detection apparatuses 120, 122, and 124. Specifically, the image display control unit 130 is connected to the radiation detection apparatuses 120, 122, and 124 via a wired or a wireless network or a dedicated line. The radiation detection apparatuses 120, 122, and 124 performs imaging of radiation generated by the radiation generation unit 112 and outputs image data to the image display control unit 130. The image display control unit 130 includes an application function operating on a computer. The image display control unit 130 outputs an image or a graphical user interface to the display unit 132 while controlling the operations of the radiation detection apparatuses 120, 122, and 124.

The image display control unit 130 controls a radiation generation timing and a radiation imaging condition of the radiation generation unit 112. The image display control unit 130 controls timings of the radiation detection apparatuses 120, 122, and 124 capturing and outputting image data. The image display control unit 130 controls the radiation detection apparatuses 120, 122, and 124 to execute imaging simultaneously and output image data simultaneously.

The image display control unit 130 executes image processing, such as noise reduction, on the image data output from the radiation detection apparatuses 120, 122, and 124. The image display control unit 130 can execute image processing, such as trimming or rotating, on the images output from the radiation detection apparatuses 120, 122, and 124. The display unit 132 displays the image output from the image display control unit 130.

The subject 100 stands on a platform placed on the imaging table 110, so that a position thereof is fixed with respect to the radiation detection apparatuses 120, 122, and 124 and the radiation generation unit 112. In the present exemplary embodiment, an irradiation angle is set such that the radiation is vertically incident on the central portion of the radiation detection apparatus 122. The radiation emitted from the radiation generation unit 112 to the radiation detection apparatuses 120, 122, and 124 passes through the subject 100 to reach the radiation detection apparatuses 120, 122, and 124, and is thus detected thereby. The image display control unit 130 executes combining processing of the pieces of image data acquired by the radiation detection apparatuses 120, 122, and 124, so that a combined image of the subject 100 is generated. The combined image is acquired through long-length imaging having a wide observation area. The display unit 132 displays the combined image output from the image display control unit 130.

The radiation imaging system can execute long-length imaging in which the entirety of the spine, the lower limb, or the body of the subject 100 is captured by a single irradiation of radiation. The radiation detection apparatuses 120, 122, and 124 (irradiation range 114) are irradiated with radiation emitted from the radiation generation unit 112 simultaneously. The operator can control a diaphragm for shielding radiation or adjusts a distance between the radiation detection apparatuses 120, 122, and 124 and the radiation generation unit 112.

The radiation detection apparatuses 120, 122, and 124 can include a detection function of automatically detecting the radiation emitted from the radiation generation unit 112. The detection function of automatically detecting emission of the radiation is a function enabling the radiation detection apparatuses 120, 122, and 124 to detect radiation and store electric charges caused by the radiation when radiation is emitted from the radiation generation unit 112. When any one of the radiation detection apparatuses 120, 122, and 124 detects the emitted radiation, the radiation detection apparatuses 120, 122, and 124 start real reading operation to acquire image data.

Figure 2:
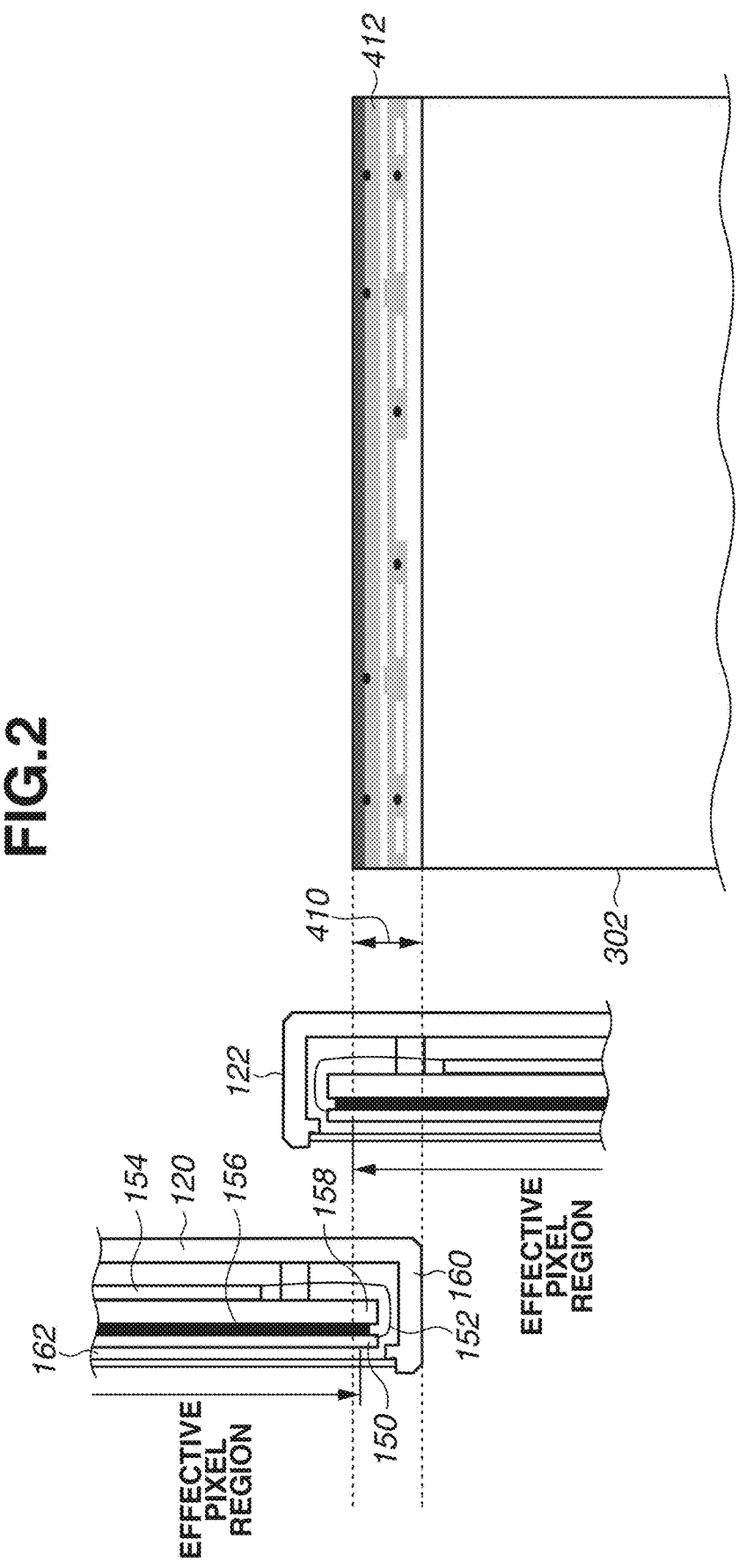
FIG. 2 is a diagram illustrating a relationship between a radiation detection apparatus of the radiographic imaging system and image data.

In the above-described radiation imaging system, the radiation detection apparatus 122 is arranged on the backside of the radiation detection apparatuses 120 and 124 in an overlapping state. Therefore, image data output from the radiation detection apparatus 122 includes a region (defective region) in which a structural object (structural information) such as a radiation detection panel, a substrate, or a housing as an internal constituent element of the radiation detection apparatus 120 or 124 included. The defective region will be described with reference to FIG. 2, which illustrates a relationship between the radiation detection apparatuses of the radiographic imaging system of the present disclosure and a radiographic image.

The radiation detection apparatus 120 includes a complex body in which a radiation detection panel 150 for detecting radiation, an adhesive member 156 for adhering and setting the radiation detection panel 150 to a panel base plate 158, the panel base plate 158 for supporting the radiation detection panel 150, and a control board 154 for making the radiation detection panel 150 output an electric signal are stacked in this order from a side of a radiation incidence surface. The radiation detection panel 150 and the control board 154 are connected via a flexible substrate 152.

An exterior housing of the radiation detection apparatus 120 is configured of a metallic housing 160 made of metal and a radiation transmission unit 162 configured of a radiation transmission member that transmits radiation. The radiation transmission unit 162 is arranged on the radiation incident surface of the radiation detection panel 150 to suppress attenuation of radiation emitted from the radiation generation unit 112. The radiation detection panel 150 includes an effective pixel region where radiation is detectable and a peripheral portion at the outer circumference of the effective pixel region.

The configuration of the radiation detection apparatus 122 or 124 is similar to that of the radiation detection apparatus 120, and thus description thereof will be omitted.

The radiation detection apparatus 122 is arranged so that a part of the effective pixel region thereof overlaps with the effective pixel region of the radiation detection apparatus 120, and thus image information can be reliably acquired by either of the effective pixel regions of the radiation detection apparatuses 120 and 122 at any line. The combined image is generated from the image data (radiographic image) output from the radiation detection apparatus 120 and image data (radiographic image) of the image region of the image data output from the radiation detection apparatus 122 which is not acquired by the radiation detection apparatus 120.

In this image generation process, the structural object of the radiation detection apparatus 120 included in image data 302 acquired from the radiation detection apparatus 122. A region 410 from an end portion of the effective pixel region of the radiation detection apparatus 122 to an end portion of the exterior housing thereof is a region where the structural object of the radiation detection apparatus 120 is included in the image data acquired from the radiation detection apparatus 122. The image data 302 acquired from the radiation detection apparatus 122 includes a defective region 412 caused by the inclusion of a structural object of the radiation detection apparatus 120. Consequently, the defective region 412 also occurs in the combined image that the combining processing unit 142 generates from the image data 302 acquired from the radiation detection apparatus 122.

In the defective region 412 of the image data 302 acquired from the radiation detection apparatus 122, a part of the radiation detection panel 150, the flexible substrate 152, the adhesive member 156, the panel base plate 158, and the metallic housing 160 of the radiation detection apparatus 120 are included as image information. Image information of a substrate or a screw on the flexible substrate 152 is included in the defective region 412.

The defective region caused by the inclusion of structural object of the radiation detection apparatus 124 occurs in the image data 302 acquired from the radiation detection apparatus 122, although it is not illustrated.

As described above, the defective region is a loss of image information caused by the structural object having a low radiation transmissivity, and information about the subject 100 is lost from the defective region. Therefore, this can lead to hindrance to diagnosis using the combined image.

Figure 3:
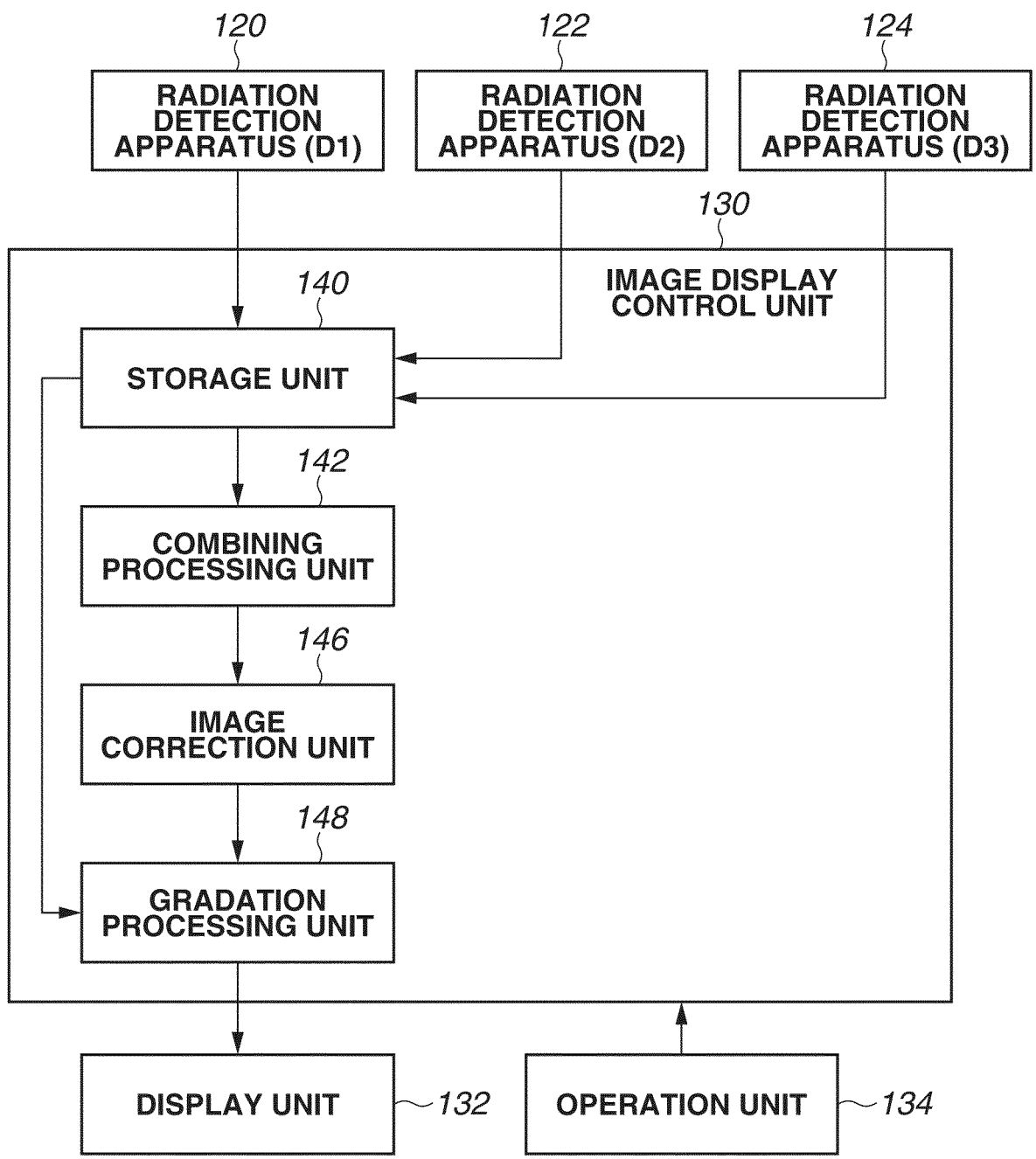
FIG. 3 is a block diagram illustrating a configuration of the radiographic imaging system (mainly an image display control unit).

An exemplary embodiment that improves the image quality by reducing the above-described defective region of the combined image caused by the overlapped radiation detection apparatuses will now be described with reference to the configuration diagram of the radiographic imaging system illustrated in FIG. 3.

The image display control unit 130 includes a storage unit 140 for storing image data output from the radiation detection apparatuses 120, 122, and 124, a combining processing unit 142 for combining image data and generating a combined image, an image correction unit 146 for correcting the inclusion of a structural object (defective region) occurring in the combined image to make the defective region unnoticeable, and a gradation processing unit 148 for executing gradation processing on the combined image corrected by the image correction unit 146.

The storage unit 140 stores image data (radiographic image) output from the radiation detection apparatuses 120, 122, and 124. As illustrated in FIG. 3, the radiation detection apparatuses 120, 122, and 124 are expressed as radiation detection apparatuses D1, D2, and D3 respectively.

The storage unit 140 can store the image data output from the radiation detection apparatuses 120, 122, and 124 together with time information. Therefore, based on the time information indicating the acquisition time of the radiographic image, the storage unit 140 can store the radiographic images such that whether the radiographic images output from the radiation detection apparatuses 120, 122, and 124 are acquired simultaneously is distinguishable. The storage unit 140 can store the radiographic image such that whether the radiographic image includes the image information of the subject 100 is distinguishable.

The storage unit 140 can store a plurality of radiographic images simultaneously captured by the radiation detection apparatuses 120, 122, and 124 in association with position information (spatial arrangement information) of the radiation detection apparatuses 120, 122, and 124. For example, the storage unit 140 can store the image data in association with information indicating that the image data output from the radiation detection apparatus 120 and the image data output from the radiation detection apparatus 122 are adjacent to each other. Similarly, the storage unit 140 can store the image data in association with the information indicating that the image data output from the radiation detection apparatus 122 and the image data output from the radiation detection apparatus 124 are adjacent to each other. The storage unit 140 can store the image data in association with the information indicating that the radiation detection apparatus 122 is arranged on the backside of the radiation detection apparatuses 120 and 124. The storage unit 140 can output a plurality of pieces of image data and position information respectively associated with the plurality of pieces of image data to the combining processing unit 142.

The combining processing unit 142 combines the plurality of pieces of image data stored in the storage unit 140 to generate a combined image. At this process, the combining processing unit 142 combines a plurality of pieces of image data which includes image information of the subject 100 to generate the combined image.

The combining processing unit 142 executes combining processing based on the plurality of pieces of image data output from the radiation detection apparatuses 120, 122, and 124, the time information, and the position information to generate the combined image. Specifically, the combining processing unit 142 identifies a plurality of pieces of image data (radiographic images) simultaneously output from the radiation detection apparatuses 120, 122, and 124 as combining targets based on the time information, and combines the plurality of pieces of image data. The combining processing unit 142 determines a positional relationship between the plurality of pieces of image data output from the radiation detection apparatuses 120, 122, and 124 based on the position information and combines the image data.

For example, in the example illustrated in FIG. 1, the image data output from the radiation detection apparatus 120 is positioned on the upper side, the image data output from the radiation detection apparatus 124 is positioned on the lower side, and the image data output from the radiation detection apparatus 122 is positioned therebetween. The combining processing is executed while the overlapping state indicated by the position information is also taken into consideration. For example, the defective regions occur in the upper portion and the lower portion of the image data output from the radiation detection apparatus 122 that is arranged at a position farther from the radiation generation unit 112 to overlap with the radiation detection apparatuses 120 and 124. However, the defective region does not occur in the image data output from the radiation detection apparatus 120 or 124. Therefore, in a range where the radiation detection apparatus 122 overlaps with the radiation detection apparatus 120 or 124, the combining processing unit 142 generates a combined image using the image data generated by the radiation detection apparatus 120 or 124 to minimize the size of the defective region occurring in the combined image. As described above, the combining processing unit 142 can generate the combined image by combining a plurality of pieces of image data acquired by capturing a plurality of adjacent imaging regions.

The image correction unit 146 executes processing of correcting the defective region and making the defective region unnoticeable on the combined image output from the combining processing unit 142. Specifically, the image correction unit 146 corrects the defective region by using structural information indicating the structural object of the radiation detection apparatus and a pixel value distribution of a normal region adjacent to the defective region. In other words, the image correction unit 146 corrects the defective region (defective row) of the combined image by using the information about a normal image region (a plurality of normal rows) adjacent to the defective region.

Herein, the structural information refers to the information indicating a structural object of a radiation detection apparatus likely to be included in a radiographic image. Information about a radiation attenuation coefficient, a thickness, and a position of a material existing inside the radiation detection apparatus is included in the structural information. When the defective region of the combined image is to be corrected, it is expected that an edge of the defective region is correlated with a pixel value distribution of a normal region spatially adjacent thereto if the structural object is not included in the defective region. Accordingly, the image correction unit 146 can reduce the defective region by executing correction for approximating the pixel value distribution of the defective region to the pixel value distribution of the normal region while taking the structural information of a radiographic image including the inclusion of the structural object into consideration.

Herein, for the sake of simplicity, a method using the image data captured by the overlapped radiation detection apparatuses 120, 122, 124 without having the subject 100 as the structural information will be described. In the structural information, the inclusion of a structural object of the radiation detection apparatus is expressed in a form of a pixel value. For example, the pixel value is small when a pixel includes the inclusion of a structural object that is thick and has a large radiation attenuation coefficient. The pixel value is large when a pixel includes the inclusion of a structural object that is thin and has a small radiation attenuation coefficient.

Figure 4:
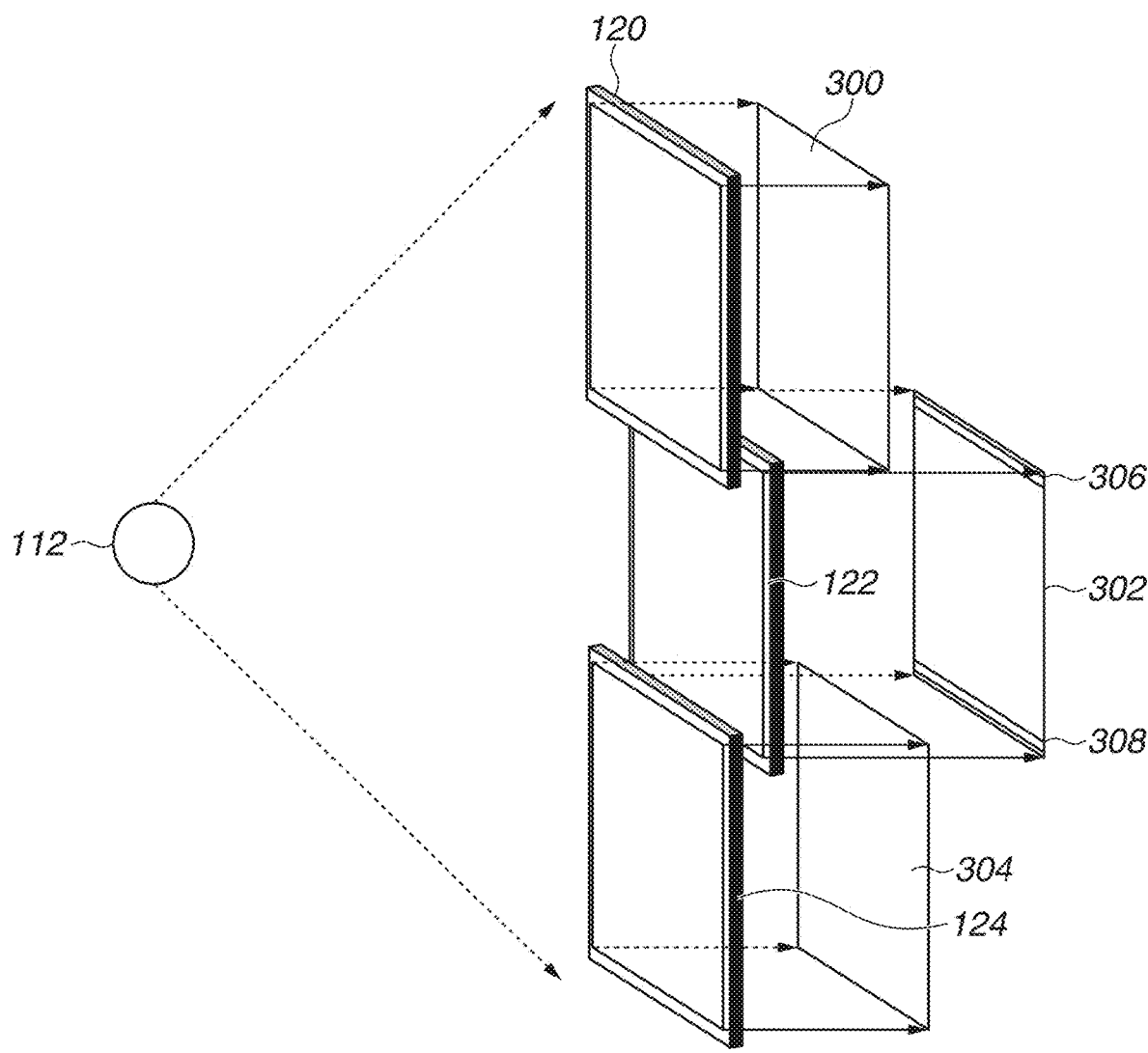
FIG. 4 is a diagram illustrating a defective region of a combined image of the radiographic imaging system.

The image data including the structural information will be described with reference to FIG. 4. FIG. 4 is a diagram schematically illustrating a configuration of the radiation imaging system of the present disclosure and a form of image data (including a defective region). When the radiation detection apparatuses 120, 122, and 124 are arranged as illustrated in FIG. 4, and imaging is executed without the subject 100, structural information of the radiation detection apparatuses 120 and 124 is included in the image data 302 acquired from the radiation detection apparatus 122.

Specifically, the image data 302 acquired from the radiation detection apparatus 122 includes an inclusion region 306 of the structural information of a lower end portion of the overlapped radiation detection apparatus 120. The image data 302 acquired from the radiation detection apparatus 122 includes an inclusion region 308 of the structural information of an upper end portion of the overlapped radiation detection apparatus 124.

In image data (radiographic image) 300 acquired from the radiation detection apparatus 120, the inclusion of other radiation detection apparatuses in structure information does not occur. In the image data (radiographic image) 304 acquired from the radiation detection apparatus 124, the inclusion of other radiation detection apparatuses in structure information does not occur. Therefore, the image data 302 corresponds to structural data that includes an inclusion state in the image as position/pixel value information. The inclusion regions 306 and 308 can be also regarded as the structural information.

While a position of the defective region in the combined image can be acquired from position information of the radiation detection apparatus stored in the storage unit 140, the position thereof can be also acquired using the structural information. In other words, when a loss of information occurring in the combined image indicated by the structural information is detected in the combined image, that detected region is regarded as a defective region. For example, in a case where the above-described inclusion regions 306 and 308 are used as the structural information, the image correction unit 146 uses the structural information as a template image to execute template matching on the combined image. Then, the image correction unit 146 acquires a position having the highest correlation as a defective region and sets that defective region as a correction target.

FIGS. 5A, 5B, and 5C are diagrams illustrating correction processing executed by the image correction unit 146 of the radiation imaging system of the present disclosure. In particular, the diagrams illustrate processing for reducing the inclusion of structural object of the radiation detection apparatuses 120 and 124 from the image data.

FIG. 5A is a diagram illustrating a combined image 510 generated by the combining processing unit 142 using a plurality of pieces of image data (radiographic images). The combined image 510 is generated and output to the image correction unit 146 by the combining processing unit 142.

FIG. 5B is a diagram illustrating an example of the structural information used for the correction processing executed by the image correction unit 146. In the present exemplary embodiment, the image data 302 that is captured without the subject 100 and acquired from the radiation detection apparatus 122 is used as the structural information. Image data acquired from the radiation detection apparatus 122 is previously stored in the storage unit 140 as gain data.

FIG. 5C is a diagram illustrating a corrected combined image 512 after the defective regions of the combined image 510 in FIG. 5A in which the structural objects of the radiation detection apparatuses 120 and 124 are included are corrected. The corrected combined image 512 is an output of the image correction unit 146. An image 500 in FIG. 5A is image data output from the radiation detection apparatus 120 that mainly includes the subject's 100 head and shoulder. An image 502 in FIG. 5A is image data output from the radiation detection apparatus 122 that mainly includes the subject's 100 body and arms. Structural information of each of the radiation detection apparatuses 120 and 124 is respectively included in the upper end portion and the lower end portion of the image 502 that cause defective regions. Based on the arrangement relationship between the radiation detection apparatuses 120, 122, and 124, the combining processing unit 142 combines the image data to minimize a size of the defective region included in the combined image.

An image 504 in FIG. 5A is image data output from the radiation detection apparatus 124 which mainly includes a leg portion of the subject 100.

As illustrated in FIG. 5A, the combining processing unit 142 combines the images 500, 502, and 504 to generate a combined image 510 to acquire an image of the subject's 100 entire body.

As illustrated in FIG. 5C, with respect to the combined image 510 illustrated in FIG. 5A, the image correction unit 146 executes correction processing for reducing the defective region caused by the inclusion of structural object of the radiation detection apparatus 120 or 124. The image correction unit 146 executes processing for differentiating the structural information serving as the image data 302 (gain data) from the combined image 510 generated from the images 500, 502, and 504 to reduce the inclusion of structural objects of the radiation detection apparatuses 120 and 124. In other words, the image correction unit 146 generates a combined image 512 in which a region (defective region) in which a part of the radiation detection apparatus 120 or 124 (a structural object of the radiation detection apparatus 120 or 124) is included is corrected.

Figure 6:
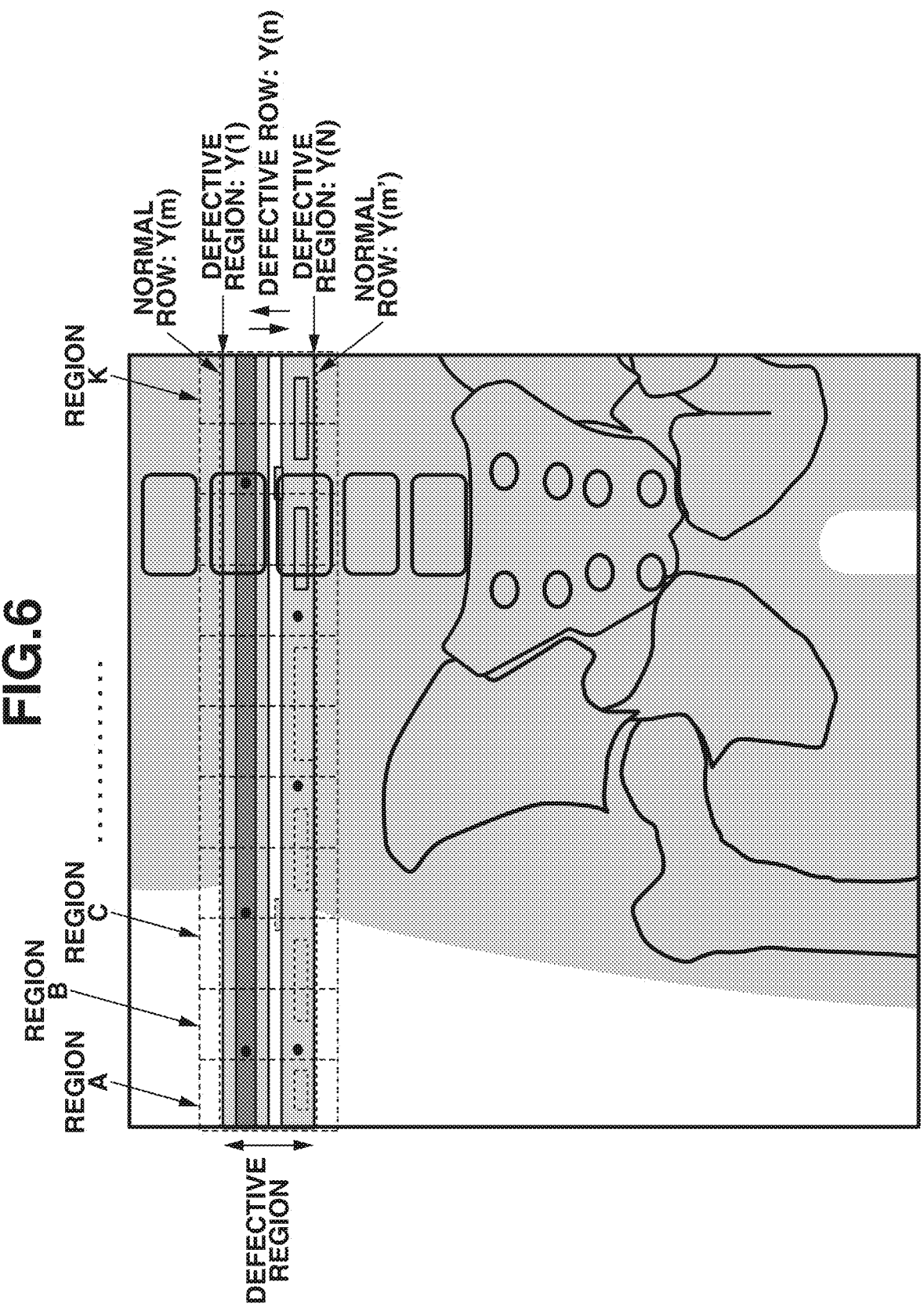
FIG. 6 is a diagram illustrating an example of correction processing executed by the image correction unit of the radiographic imaging system.
Figure 8:
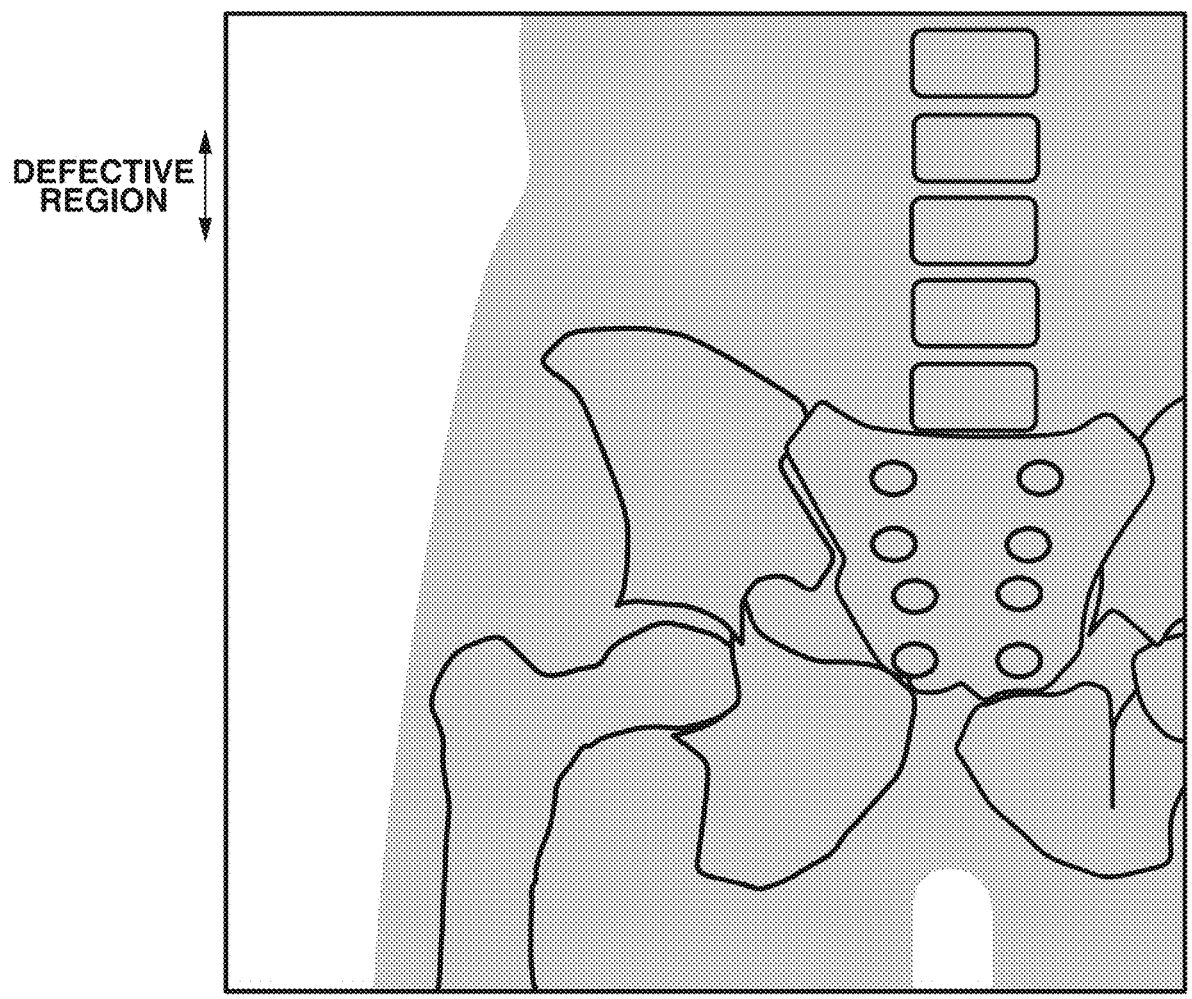
FIG. 8 is a diagram illustrating an image after the correction processing is executed by the image correction unit of the radiographic imaging system.

Correction processing executed by the image correction unit 146 after executing the above-described differentiating processing will be described with reference to FIG. 6, FIGS. 7A to 7C, and FIG. 8. FIG. 6 is a diagram illustrating an enlarged view of a dashed-line region 600 in FIG. 5A, and FIG. 8 is a diagram illustrating an enlarged view of a dashed-line region 700 in FIG. 5C.

As illustrated in FIG. 6, in a plurality of correction regions (regions A to K) sectioned in a column direction, the image correction unit 146 corrects a defective row of a region (defective region), where the structural object of the radiation detection apparatus is included in the combined image, by using a normal row including a normal image region adjacent to the defective row. In each of the correction regions, the image correction unit 146 corrects the defective row by combining a radiographic image of the normal row into a radiographic image of the defective row while making the correlation between the radiographic image of the normal row and the radiographic image of the defective row. The image correction unit 146 executes registration between the defective region of the combined image and structural information, and corrects the combined image by using the defective information included in the structural information corresponding to the defective row of the combined image.

As illustrated in FIG. 6, a range of the defective region as a correction target of the image correction unit 146 is specified by row numbers, such as a row Y(1) to a row Y(N), in the combined image. A row Y(n) of the defective region ("n" satisfies "1≤n≤N") is referred to as a defective row. Rows Y(m) and Y(m') of the normal region adjacent to the rows Y(1) and Y(N) as ending rows of the defective region are referred to as normal rows. A plurality of regions A to K sectioned in the column direction with respect to the defective region is referred to as correction regions.

As illustrated in FIG. 6, the image correction unit 146 executes correction processing of the defective region for each of the correction regions. Specifically, in each correction region of the regions A to K, the image correction unit 146 corrects the defective row one by one using the normal rows adjacent thereto. The corrected defective row is regarded as a new normal row and used for correcting the subsequent defective row. Processing of individually correcting the defective row into the normal row is repeatedly executed, so that the entire defective region is processed and corrected. In other words, in each of the correction regions of the regions A to K, the image correction unit 146 divides the defective region of the combined image into a row unit of defective rows. Then, for each of the rows from the ending row of the defective region, the image correction unit 146 repeatedly executes the correction processing for approximating a pixel value distribution of the defective row to a pixel value distribution of the normal row as a part of the normal region adjacent to an ending row, or to a pixel value distribution of a corrected defective row.

For example, when correction is executed from a top to a bottom of the image for each correction region of the regions A to K, the defective row Y(1) is corrected using the normal row Y(m). Then, the defective row Y(2) is corrected using the corrected defective row Y(1) as a normal row. Accordingly, when "n" satisfies "1≤n≤N", correction of the defective row Y(n) can be sequentially executed using a row Y(n−1) as a normal row. When correction is to be executed from the bottom to the top, correction of the defective row Y(N) is sequentially executed using the row Y(m') as a normal row.

The above-described correction processing can be executed by any method using a correlation between the adjacent pixels of each correction region of the regions A to K.

The image correction unit 146 can also correct the defective region in a pixel unit. For example, coordinates of an x-th pixel in the row Y(n) of the combined image ("x" satisfies "1≤x≤W") is expressed as (x, Y(n)), and a pixel value in that coordinates (x, Y(n)) before making correction is expressed as I(x, Y(n)). Then, a pixel value O(x, Y(n)) in that coordinates (x, Y(n)) after making correction is expressed by the following formula:

$$O(x,Y(n))=f(I(x,Y(n))|\beta_x^*), \beta_x^*=(b_{x,1},b_{x,2},\ldots,b_{x,k}),$$

where a function "f" is a function having k-pieces of model parameters $\beta_x^*$, and the model parameter $\beta_x^*$ is acquired by solving a least-square optimization formula expressed as follows:

$$\beta_x^* = \underset{\beta_x}{\operatorname{argmin}} \sum_{j=-D}^{+D} \{I(x+j, Y(m)) - f(I(x+j, Y(n)) | \beta_x)\}^2, \quad (1)$$

where "Y(m)" represents a normal row adjacent to the row Y(n). For example, the function "f" is expressed by a polynomial equation, and a polynomial coefficient (model parameter) is acquired by the least-square method, so that a function for converting a defective row into a normal row can be acquired for each row. The image correction unit 146 can execute correction in a predetermined pixel range (pixel range of ±D) using this function to calculate the formula 1.

Alternatively, the image correction unit 146 can execute correction by using structural data of the structural object of the radiation detection apparatus included in the combined image. A pixel value in the structural data corresponding to the coordinates (x, Y(n)) is expressed as P(x, Y(n)). In other words, the pixel value P(x, Y(n)) in the structural data includes information relating to the structural object of the radiation detection apparatus included in the pixel having the pixel value I(x, Y(n)) of the combined image. In this case, the pixel value O(x, Y(n)) of the coordinates (x, Y(n)) after making correction is expressed by the following formula:

$$O(x, Y(n)) = g(I(x, Y(n)), P(x, Y(n)) | \beta_x^*), \beta_x^* = (b_{x,1}, b_{x,2}, \ldots, b_{x,k}) \quad (2),$$

where "$\beta_x^*$" represents k-pieces of model parameters, and a parameter that makes an error between the row Y(n) and the normal row Y(m) adjacent to the row Y(n) become a minimum is calculated by the least-square method. In other words, the model parameter $\beta_x^*$ is used as a correction value of the pixel value of the correction target pixel. The image correction unit 146 executes correction by modeling a relationship between the pixel value O(x, Y(n)) after making correction, the pixel value I(x, Y(n)) before making correction, and the pixel value P(x, Y(n)) in the structural data by using a function "g" through the formula 2.

FIGS. 7A, 7B, and 7C are diagrams schematically illustrating correction of the correction target pixel (x, P(n)) executed by the image correction unit 146. For example, as illustrated in FIG. 7A, when the correction target pixel (x, P(n)) is to be corrected, the image correction unit 146 executes correction by calculating the appropriate model parameter $\beta_x^*$ in a predetermine region in a range of ±D in a column direction from the correction target pixel (x, P(n)).

Herein, "$\beta_x^*$" represents a model parameter for correcting a pixel of an x-th column, and the model parameter $\beta_x^*$ is calculated by the following formula with reference to the peripheral pixels of the correction target pixel (x, P(n)). The image correction unit 146 calculates a local optimum solution (pixel value) for each pixel by calculating the model parameter $\beta_x^*$ that makes an error become a minimum in a predetermined range (i.e., a range of ±D).

$$\beta_x^* = \underset{\beta_x}{\arg\min} \sum_{j=-D}^{+D} \{I(x+j, Y(m)) - g(I(x+j, Y(n)), P(x+j, Y(n)) | \beta_x)\}^2 \quad (3)$$

As described above, correction is executed by the model parameter $\beta_x^*$ acquired at a local region having the correction target pixel (x, P(n)) at the center, so that the pixel value of the correction target pixel (x, P(n)) can be corrected by the appropriate model parameter $\beta_x^*$.

In other words, the image correction unit 146 calculates the model parameter $\beta_x^*$ for the region having the correction target pixel (x, P(n)) at the center, and can correct the pixel value of the correction target pixel (x, P(n)) using the calculated model parameter $\beta_x^*$. Therefore, the image correction unit 146 corrects the pixel value of the correction target pixel (x, P(n)) by using a pixel value of the pixel in a predetermined range having the correction target pixels (x, P(n)) at the center. In the present exemplary embodiment, the pixel value of the correction target pixel (x, P(n)) is calculated to minimize an error between the defective row Y(n) and the normal row Y(m) adjacent to the defective row Y(n).

As illustrated in FIG. 7B, when the correction target pixel (1, P(n)) is in a first column, the image correction unit 146 calculates a model parameter $\beta_x^*$ to minimize an error in a range of the first column to the (1+D)-th column based on the formula 3 to calculate a local optimum solution for the correction target pixel (1, P(n)).

As illustrated in FIG. 7C, when the correction target pixel (3, P(n)) is positioned at a third column, the image correction unit 146 calculates a model parameter $\beta_x^*$ to minimize an error in a range of the first column to the (3+D)-th column based on the formula 3 to calculate a local optimum solution for the correction target pixel (3, P(n)). In other words, the image correction unit 146 corrects the correction target pixel (x, P(n)) using the first column to the (x+D)-th column or in a range of the (x−D)-th column to the W-th column, based on a position of the peripheral pixel of the correction target pixel (x, P(n)) in a region where the structural object is not included in the combined image.

As described above, the image correction unit 146 executes processing for pixel by pixel while shifting an execution position to the right as illustrated in FIGS. 7A to 7C to process all of the pixel values of the defective row Y(n). With this processing, a pixel value of the correction target pixel (x, P(n)) of the defective row Y(n) can be acquired. The image correction unit 146 continuously executes processing on the Y(n+1)-th row to eventually process the rows in the region where the structural object is included. The image correction unit 146 executes correction to make a pixel value of the region where the structural object is included and a pixel value of the region where the structural object is not included become substantially the same.

The image correction unit 146 can combine results of correction executed in both the upper and lower directions instead of using a result of correction executed in only one direction. The image correction unit 146 generates two correction results to correct the combined image by executing correction in both the upper and the lower directions from the upper row and the lower row adjacent to the defective region of the combined image on the upper side and the lower side thereof. For example, the image correction unit 146 generates two pieces of image data, i.e., image data of a defective region corrected from the upper side and image data of the defective region corrected from the lower side. A defective row corrected from the upper side and a defective row corrected from the lower side are the same row in the defective region (overlapped region). Specifically, the image correction unit 146 corrects the image data of the defective row by taking an average of the image data of the defective row corrected from the upper side and the image data thereof corrected from the lower side. Correction accuracy is normally higher when the corrected defective row is closer to the normal row adjacent to the end of the defective region. Thus, the correction results can be combined while weight based on a distance from the correction starting row is taken into consideration. In this case, for example, when a row number of the defective region is "N−1", a result of correction from the upper side is "O1", and a result of correction from the lower side is "O2", a correction result O(n) of the n-th row can be expressed by the following formula.

$$O(x, Y(n)) = \frac{(N-1-n)}{N-1} O1(x, Y(n)) + \frac{n}{N-1} O2(x, Y(n)) \qquad (4)$$

FIG. 8 is a diagram illustrating a combined image after correction displayed on the display unit 132. By correcting a defective region (overlapped region) to correct the combined image, the inclusion of the structural object of the radiation detection apparatus in the combined image is reduced, so that image quality of the combined image can be improved.

The gradation processing unit 148 executes gradation processing on the combined image acquired by combining a plurality of pieces of image data (radiographic image). Specifically, the gradation processing unit 148 acquires a plurality of pieces of image data acquired from the radiation detection apparatuses 120, 122, and 124 from the storage unit 140. The gradation processing unit 148 analyzes feature quantities of the plurality of pieces of image data acquired from the radiation detection apparatuses 120, 122, and 124, and determines a gradation conversion characteristic of the combined image to effectively use a dynamic range of the display unit 132.

Then, the gradation processing unit 148 convers the gradation of the combined image by using the determined gradation conversion characteristic. A histogram, a maximum pixel value, and a minimum pixel value of each image data are included in the feature quantity, and the gradation processing unit 148 calculates the feature quantity by executing analysis processing on the plurality of pieces of image data acquired from the radiation detection apparatuses 120, 122, and 124.

The gradation processing unit 148 can execute gradation processing on the combined image corrected by the image correction unit 146. As described above, because the gradation processing is executed on the combined image where the defective region is reduced, gradation processing of the combined image can be appropriately executed. In other words, the gradation processing unit 148 can execute the gradation processing of the combined image while suppressing the effect of the inclusion of the structural objects of the radiation detection apparatuses 120 and 124.

The display unit 132 can display the combined image where the defective region is reduced. In other words, the image quality of the combined image in which a structural object of the radiation detection apparatus is included can be improved.

Next, an operation procedure of the radiation imaging system will be described with reference to the flowchart in FIG. 9.

In step S801, the operator arranges the plurality of radiation detection apparatuses 120, 122, and 124 on the imaging table 110. The operator arranges each of the radiation detection apparatuses 120, 122, and 124 in the lengthwise direction of the imaging table 110. In this arrangement, the operator arranges the radiation detection apparatuses 120, 122, and 124 to overlap a part of the radiation detection apparatuses 120, 122, and 124 with each other so that the effective pixel regions where radiation is detectable overlap with each other.

In step S802, the operator operates the radiation detection apparatuses 120, 122, and 124 to simultaneously execute imaging and the radiation detection apparatuses 120, 122, and 124 simultaneously output a plurality of pieces of image data to the combining processing unit 142. The combining processing unit 142 combines the image data to generate a combined image.

In step S803, the operator operates the operation unit 134 to select whether to execute correction processing on the combined image. For example, if the defective region in which the structural object of the radiation detection apparatus is included is not included in the diagnosis region, the correction processing does not have to be executed. In a case where the correction processing of the combined image is not executed (NO in step S803), the processing proceeds to step S805. In a case where the correction processing of the combined image is to be executed (YES in step S803), the processing proceeds to step S804.

In step S804, the image correction unit 146 executes processing of reducing the defective region caused by the inclusion of the structural objects of the radiation detection apparatuses 120 and 124 on the combined image output from the combining processing unit 142. In the present exemplary embodiment, the image correction unit 146 corrects a pixel value of the correction target pixel (x, P(n)) of a region in the combined image in which the structural object of the overlapped radiation detection apparatus is included using a pixel value of a pixel of a peripheral pixel, which is within a range of ±D having the correction target pixel at the center, in a region in the combined image in which the structural object is not included.

In step S805, the gradation processing unit 148 executes gradation processing on the combined image output from the combining processing unit 142. Alternatively, the gradation processing unit 148 executes gradation processing on the combined image corrected by the image correction unit 146.

As described above, according to the present exemplary embodiment, the image correction unit 146 corrects a pixel value of the correction target pixel (x, P(n)) of the region in which the structural object of the overlapped radiation detection apparatus is included in the combined image using pixel values of pixels, which are a plurality of pixels in a row direction having the correction target pixel at the center, in a range predetermined with reference to the correction target pixel (x, P(n)) of the region in which the structural objects is not included in the combined image. Therefore, improving the image quality of the combined image by appropriately correcting the region in which the structural object of the radiation detection apparatus is included is accomplished.

A second exemplary embodiment will be described with reference to FIGS. 10A and 10B. The present exemplary embodiment is different from the first exemplary embodiment in that the image correction unit 146 calculates a model parameter for each correction target section in a defective row of a defective region. Each correction target section can correspond to a different one of the regions A to K illustrated in FIG. 6.

As illustrated in FIG. 10A, when a correction target section of the region in which the structural object of the radiation detection apparatus is included in the combined image is to be corrected, the image correction unit 146 calculates model parameters $\beta_{x1}^*$ and $\beta_{x2}^*$ at two points of a starting pixel (x1, P(n)) and an ending pixel (x2, P(n)) of the correction target section using the formula 4 described in the first exemplary embodiment.

Specifically, the image correction unit 146 calculates the model parameter $\beta_{x1}^*$ that minimizes an error in a range of ±D of the starting pixel (x1, P(n)) of the correction target section, and calculates the model parameter $\beta_{x2}^*$ that minimizes an error in a range of ±D of the ending pixel (x2, P(n)) of the correction target section.

Then, the image correction unit 146 corrects a correction result obtained using the two model parameters $\beta_{x1}^*$ and $\beta_{x2}^*$ through weighted addition based on the distances to the starting pixel and the ending pixel using the following formula.

$$O(x, Y(n)) = (1 - w(x)) \cdot g(I(x, Y(n)), P(x, Y(n)) \mid \beta_{x1}^*) + \quad (5)$$
$$w(x) \cdot g(I(x, Y(n)), P(x, Y(n)) \mid \beta_{x2}^*) w(x) = \frac{x - x1}{x2 - x1}, x1 \le x \le x2$$

When the above-described correction is executed, high speed correction can be executed because calculation of the model parameters is executed twice with respect to the starting pixel and the ending pixel of the correction target section.

Similarly, the image correction unit 146 calculates the model parameters of a plurality of correction target sections in a defective row Y(n) of the defective region.

As illustrated in FIG. 10B, when a correction target section including the first column is to be corrected, the image correction unit 146 calculates the model parameters $\beta_1^*$ and $\beta_S^*$ for two points of a starting pixel (1, P(n)) and an ending pixel (S, P(n)) of the correction target section. In this case, a pixel at the first column is the starting pixel of the correction target section. When a correction target section including the W-th column is to be corrected, the image correction unit 146 calculates the model parameters $\beta_{W-S}^*$ and $\beta_W^*$ at two points of a starting pixel (W-S, P(n)) and an ending pixel (W, P(n)) of the correction target section. At this time, a pixel at the W-th column is the ending pixel of the correction target section.

As described above, the image correction unit 146 corrects a pixel value of the first correction target pixel (x, P(n)) of a region in which the structural object of the radiation detection apparatus is included using a pixel in the periphery of the first correction target pixel (x, P(n)), which is in a range of ±D having the correction target pixel at the center, in a region in which the structural object is not included in the combined image. The image correction unit 146 corrects a pixel value of the second correction target pixel (x2, P(n)) of the region in which the structural object of the radiation detection apparatus is included using a pixel in the periphery of the second correction target pixel (x2, P(n)), which is in a range of ±D having the correction target pixel at the center, in a region in which the structural object is not included in the combined image. Then, the image correction unit 146 interpolates and calculates pixel values of the pixels between the first correction target pixel (x, P(n)) and the second correction target pixel (x2, P(n)) using the corrected pixel values of the two correction target pixels (x, P(n)) and (x2, P(n)). The image correction unit 146 executes weighted addition based on the distances to the two correction target pixels (x, P(n)) and (x2, P(n)), and calculates the pixel values of the pixels between the first correction target pixel (x, P(n)) and the second correction target pixel (x2, P(n)).

A third exemplary embodiment will be described with reference to FIG. 11. The present exemplary embodiment is different from the first and the second exemplary embodiments in that the image correction unit 146 sets a plurality of correction target sections, to make correction target pixels of the correction target sections that overlap each other, to calculate the model parameter.

Figure 11:
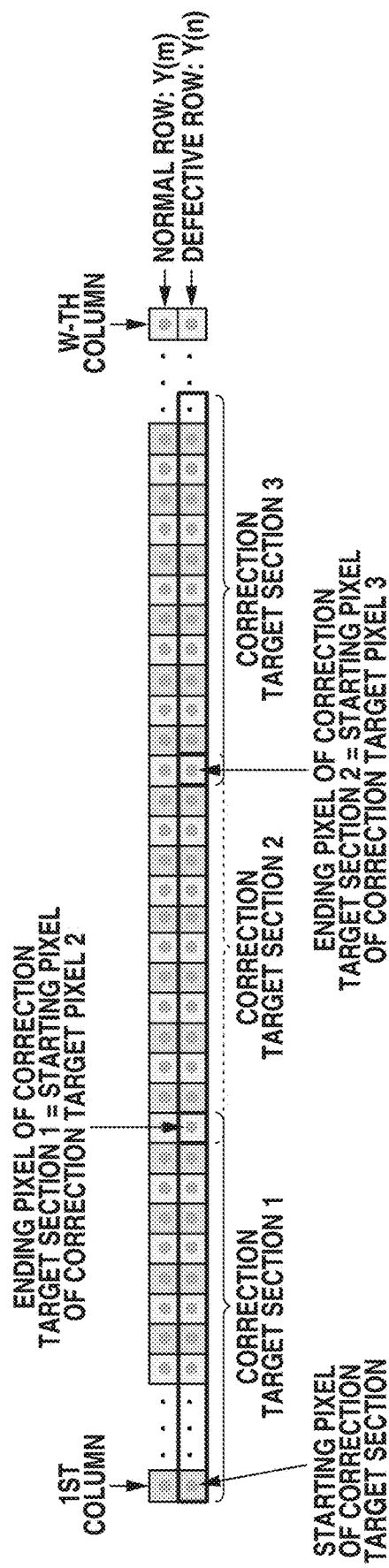
FIG. 11 is a diagram illustrating an example of correction processing executed by the image correction unit of the radiographic imaging system in a third exemplary embodiment.

As illustrated in FIG. 11, the image correction unit 146 sets the correction target sections so that the starting pixels and the ending pixels of the correction target sections overlap each other. Specifically, the image correction unit 146 calculates the model parameters $\beta_1^*$ and $\beta_S^*$ for each of the two points of a starting pixel (1, P(n)) and an ending pixel (S, P(n)) of a correction target section 1. Then, the image correction unit 146 sets the ending pixel of the correction target section 1 as a starting pixel of a correction target section 2 adjacent thereto. In the present exemplary embodiment, the image correction unit 146 calculates the model parameters $\beta_S^*$ and $\beta_{S'}^*$ for each of the two points of the starting pixel (S, P(n)) and an ending pixel (S', P(n)) of the correction target section 2. Then, the image correction unit 146 calculates the model parameters $\beta_{S'}^*$ and $\beta_{S''}^*$ for each of the two points of the starting pixel (S', P(n)) and an ending pixel (S'', P(n)) of a correction target section 3. Similarly, the image correction unit 146 sets the correction target sections so that the starting pixels and the ending pixels of the adjacent correction target sections overlap each other, and calculates the model parameters for each of the correction target sections.

According to the present exemplary embodiment, it is sufficient for the image correction unit 146 to calculate the model parameters for the number of times equivalent to "the number of correction target sections+1". Therefore, high speed correction can be executed because the number of calculation times of the model parameters is reduced.

Figure 12:
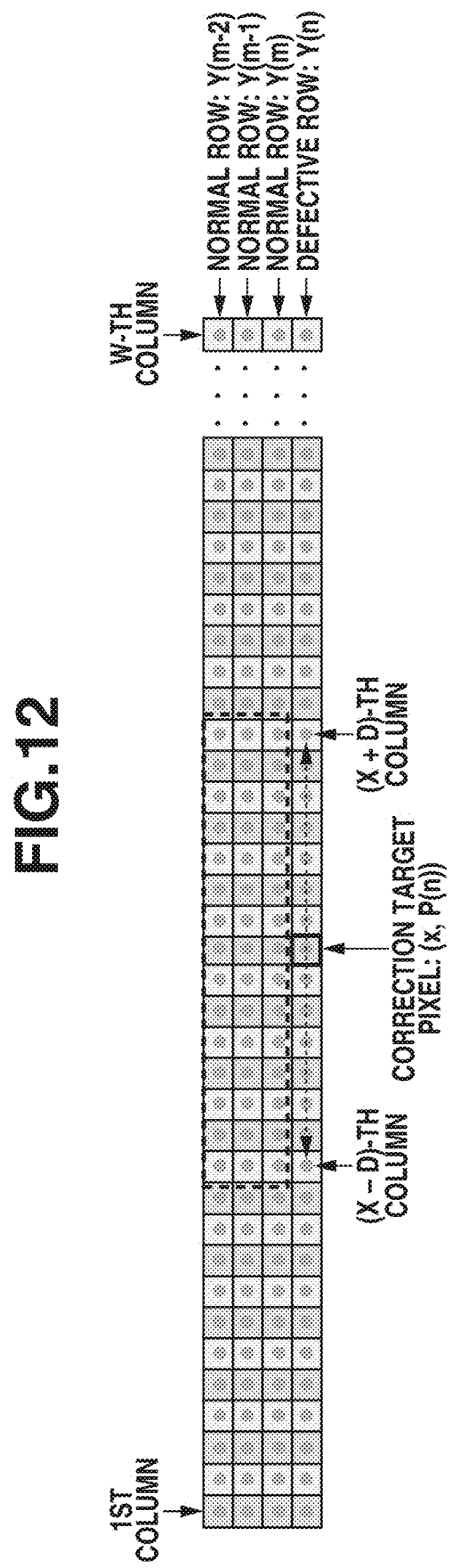
FIG. 12 is a diagram illustrating an example of correction processing executed by the image correction unit of the radiographic imaging system in a fourth exemplary embodiment.

A fourth exemplary embodiment will be described with reference to FIG. 12. The present exemplary embodiment is different from the first to the third exemplary embodiments in that the image correction unit 146 corrects a defective row of a region in which the structural object of the radiation detection apparatus is included using a plurality of normal rows of a region in which the structural object is not included, i.e., using a plurality of normal rows adjacent to the defective row. In other words, the peripheral pixels of the correction target pixel described in the first exemplary embodiment consist of a plurality of normal rows in which the structural object is not included.

With respect to the model parameter β* expressed by the formula 3 described in the first exemplary embodiment, the image correction unit 146 calculates a parameter that minimizes an error between a plurality of normal rows Y(m) to Y(m−2) adjacent to the defective row Y(n) through the least-square method. Specifically, the image correction unit 146 executes addition average processing of the pixel values on the normal rows for each column and acquires a representative pixel value of the normal rows for each column. In other words, the representative pixel value of the plurality of normal rows is calculated for each column.

The image correction unit 146 then calculates a local optimum solution for each pixel by calculating a model parameter that minimizes an error in a range of ±D described in the formula 3 of the first exemplary embodiment. In other words, the image correction unit 146 corrects a pixel value of the correction target pixel (x, P(n)) of the region in which a structural object of the overlapped radiation detection apparatus is included in the combined image using the representative pixel value of a plurality of normal rows in which the structural object is not included.

Therefore, even in a case where noise occurs in a normal row of the region in which the structural object is not included, the image correction unit 146 can stably correct a pixel value of the correction target pixel by calculating the model parameter using the representative pixel value of the plurality of normal rows.

Other Embodiments

Embodiments can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-203476, filed Oct. 17, 2016, which is hereby incorporated by reference herein in its entirety.

What is claimed is:

1. A radiographic imaging system comprising:
a plurality of radiation detection apparatuses that detect radiation; and
one or more memories storing instructions; and
one or more processors that, upon executing the instructions, are configured to
combine a plurality of radiographic images acquired from the plurality of radiation detection apparatuses to generate a combined image and to correct a pixel value of a correction target pixel of a region in which a structural object of a radiation detection apparatus is included in the combined image using a pixel value of a pixel in a range predetermined with reference to the correction target pixel of a region in which the captured structural object is not included in the combined image, to further correct a pixel value of a correction target pixel of adjacent region in which the structural object is included in the combined image using a pixel value of the corrected first correction target pixel, and to interpolate and calculate a pixel value of a pixel between a first correction target pixel and a second correction target pixel of the region in which the structural object of the radiation detection apparatus is included using corrected pixel values of the first correction target pixel and the second correction target pixel.

2. The radiographic imaging system according to claim 1, wherein execution of the instructions further configures the one or more processors to correct a pixel value of the correction target pixel using pixel values of a plurality of pixels, which is in a row direction having the correction target pixel at a center, of the region in which the structural object is not included in the combined image.

3. The radiographic imaging system according to claim 1, wherein execution of the instructions further configures the one or more processors to calculate a model parameter in a correction target section of the region in which the structural object of the radiation detection apparatus is included in the combined image, and corrects a pixel value of a correction target pixel using the calculated model parameter.

4. The radiographic imaging system according to claim 3, wherein execution of the instructions further configures the one or more processors to calculate the model parameter with respect to a plurality of correction target sections of a defective row of the region in which the structural object of the radiation detection apparatus is included.

5. The radiographic imaging system according to claim 3, wherein execution of the instructions further configures the one or more processors to, to calculate the model parameter, sets a plurality of correction target sections so that correction target pixels of the correction target sections overlap each other.

6. The radiographic imaging system according to claim 1, wherein pixels in periphery of the correction target pixel consist of a plurality of normal rows in which the structural object of the radiation detection apparatus is not included in the combined image.

7. The radiographic imaging system according to claim 1, further comprising
an imaging table on which a plurality of the radiation detection apparatuses is arranged so that parts of the plurality of radiation detection apparatuses overlap each other.

8. The radiographic imaging system according to claim 1, further comprising
a radiation generator configured to emit radiation,
wherein the plurality of radiation detection apparatuses is simultaneously irradiated with the emitted radiation.

9. A radiographic imaging system comprising
a plurality of radiation detection apparatuses that detect radiation;
one or more memories storing instructions; and
one or more processors that, upon execution of the instructions, are configured to
combine a plurality of radiographic images acquired from the plurality of radiation detection apparatuses, and
correct a defective row of a region in which a structural object of a radiation detection apparatus is included in the combined image using a plurality of normal rows of a region in which the structural object is not included by combining a radiographic image of the normal row into a radiographic image of the defective row while correlating the radiographic image of the normal row and the radiographic image of the defective row, to further correct adjacent defective row of the region in which the structural object is included in the combined image using the corrected first defective row and to interpolate and calculate a pixel value of a pixel between a first correction target pixel and a second correction target pixel of the region in which the structural object of the radiation detection apparatus is included using corrected pixel values of the first correction target pixel and the second correction target pixel.

10. The radiographic imaging system according to claim 9, wherein execution of the instructions further configures the one or more processors to divide the region in which the structural object of the radiation detection apparatus is included in the combined image into a row unit of defective rows, and for each row from an end row of the region, repeatedly executes correction processing for approximating a pixel value distribution of a defective row to a pixel value distribution of a normal row as a part of a normal region adjacent to the end row or a pixel value distribution of a corrected defective row.

11. The radiographic imaging system according to claim 9, wherein execution of the instructions further configures the one or more processors to execute positioning between the region in which the structural object of the radiation detection apparatus is included in the combined image and structural information, and corrects the combined image using defective information included in the structural information corresponding to the defective row of the combined image.

12. The radiographic imaging system according to claim 9, wherein execution of the instructions further configures the one or more processors to correct the combined image, generates two correction results by executing correction in both an upper and a lower direction from an upper row and a lower row adjacent to the defective region of the combined image on an upper side and a lower side of the defective region.

13. A radiographic imaging method for combining a plurality of radiographic images acquired from a plurality of radiation detection apparatuses to generate a combined image, the radiographic imaging method comprising:
correcting a pixel value of a correction target pixel of a region in which a structural object of a radiation detection apparatus is included in the combined image using a pixel value of a pixel in a range predetermined with reference to the correction target pixel of a region in which the structural object is not included in the combined image, further correcting a pixel value of adjacent correction target pixel of the region in which the structural object is included using a pixel value of the corrected correction target pixel, and further interpolating and calculating a pixel value of a pixel between a first correction target pixel and a second correction target pixel of the region in which the structural object of the radiation detection apparatus is included using corrected pixel values of the first correction target pixel and the second correction target pixel.

14. A radiographic imaging method for combining a plurality of radiographic images acquired from a plurality of radiation detection apparatuses to generate a combined image, the radiographic imaging method comprising:
correcting a defective row of a region in which a structural object of a radiation detection apparatus is included in the combined image using a plurality of normal rows of a region in which the structural object is not included
wherein the defective row is corrected by combining a radiographic image of the normal row into a radiographic image of the defective row while correlating the radiographic image of the normal row and the radiographic image of the defective row, further correcting adjacent defective row of the region in which the structural object is included in the combined image using the corrected first defective row and further interpolating and calculating a pixel value of a pixel between a first correction target pixel and a second correction target pixel of the region in which the structural object of the radiation detection apparatus is included using corrected pixel values of the first correction target pixel and the second correction target pixel.

15. A non-transitory computer-readable storage medium storing a program that causes a computer to perform a radiographic imaging method for combining a plurality of radiographic images acquired from a plurality of radiation detection apparatuses to generate a combined image, the radiographic imaging method comprising:
correcting a pixel value of a correction target pixel of a region in which a structural object of a radiation detection apparatus is included in the combined image using a pixel value of a pixel in a range predetermined with reference to the correction target pixel of a region in which the structural object is not included in the combined image, further correcting a pixel value of adjacent correction target pixel of the region in which the structural object is included using a pixel value of the corrected correction target pixel, and further interpolating and calculating a pixel value of a pixel between a first correction target pixel and a second correction target pixel of the region in which the structural object of the radiation detection apparatus is included using corrected pixel values of the first correction target pixel and the second correction target pixel.

16. A non-transitory computer-readable storage medium storing a program that causes a computer to perform a radiographic imaging method for combining a plurality of radiographic images acquired from a plurality of radiation detection apparatuses to generate a combined image, the radiographic imaging method comprising:
correcting a defective row of a region in which a structural object of a radiation detection apparatus is included in the combined image using a plurality of normal rows of a region in which the structural object is not included
wherein the defective row is corrected by combining a radiographic image of the normal row into a radiographic image of the defective row while correlating the radiographic image of the normal row and the radiographic image of the defective row, further correcting adjacent defective row of the region in which the structural object is included in the combined image using the corrected first defective row, and further interpolating and calculating a pixel value of a pixel between a first correction target pixel and a second correction target pixel of the region in which the structural object of the radiation detection apparatus is included using corrected pixel values of the first correction target pixel and the second correction target pixel.

* * * * *